United States Patent [19]

Dickover et al.

[11] Patent Number: 4,464,217
[45] Date of Patent: Aug. 7, 1984

[54] METHOD FOR EFFECTING SECURMENT OF ALTERNATING STRETCHED AND UNSTRETCHED ELASTIC RIBBON TO A MOVING WEB

[75] Inventors: William E. Dickover, Lyons; Ladislav J. Klasek, North Riverside; Anthony Passafiume, Burbank, all of Ill.

[73] Assignee: Johnson & Johnson Baby Products Company, New Brunswick, N.J.

[21] Appl. No.: 150,515

[22] Filed: May 16, 1980

[51] Int. Cl.³ .............................................. B32B 31/08
[52] U.S. Cl. .................................. 156/164; 156/229; 156/494; 156/495
[58] Field of Search ............... 156/164, 229, 361, 264, 156/265, 494, 522, 519, 552, 555; 226/1 R; 242/75, 75.3; 128/284 R, 287

[56] References Cited

U.S. PATENT DOCUMENTS

| | | | |
|---|---|---|---|
| 3,443,532 | 5/1969 | Posey et al. | 112/121.26 X |
| 3,495,790 | 2/1970 | Fisnar | 242/75.3 X |
| 3,828,367 | 8/1974 | Bourgeois | 156/164 |
| 4,081,301 | 3/1978 | Buell | 156/164 |
| 4,216,804 | 8/1980 | Alexander | 242/75 |
| 4,239,578 | 12/1980 | Gore | 156/164 |
| 4,240,866 | 12/1980 | Rega | 156/519 |

Primary Examiner—David A. Simmons

[57] ABSTRACT

This invention relates to a method for the continuous or intermittent securing of a moving elastic member or band to a moving web or webs of disposable diaper components and the like, wherein at least one component is provided with an alternating sequence of stretchable or elastic portions and non-stretchable, inelastic portions along its length.

12 Claims, 19 Drawing Figures

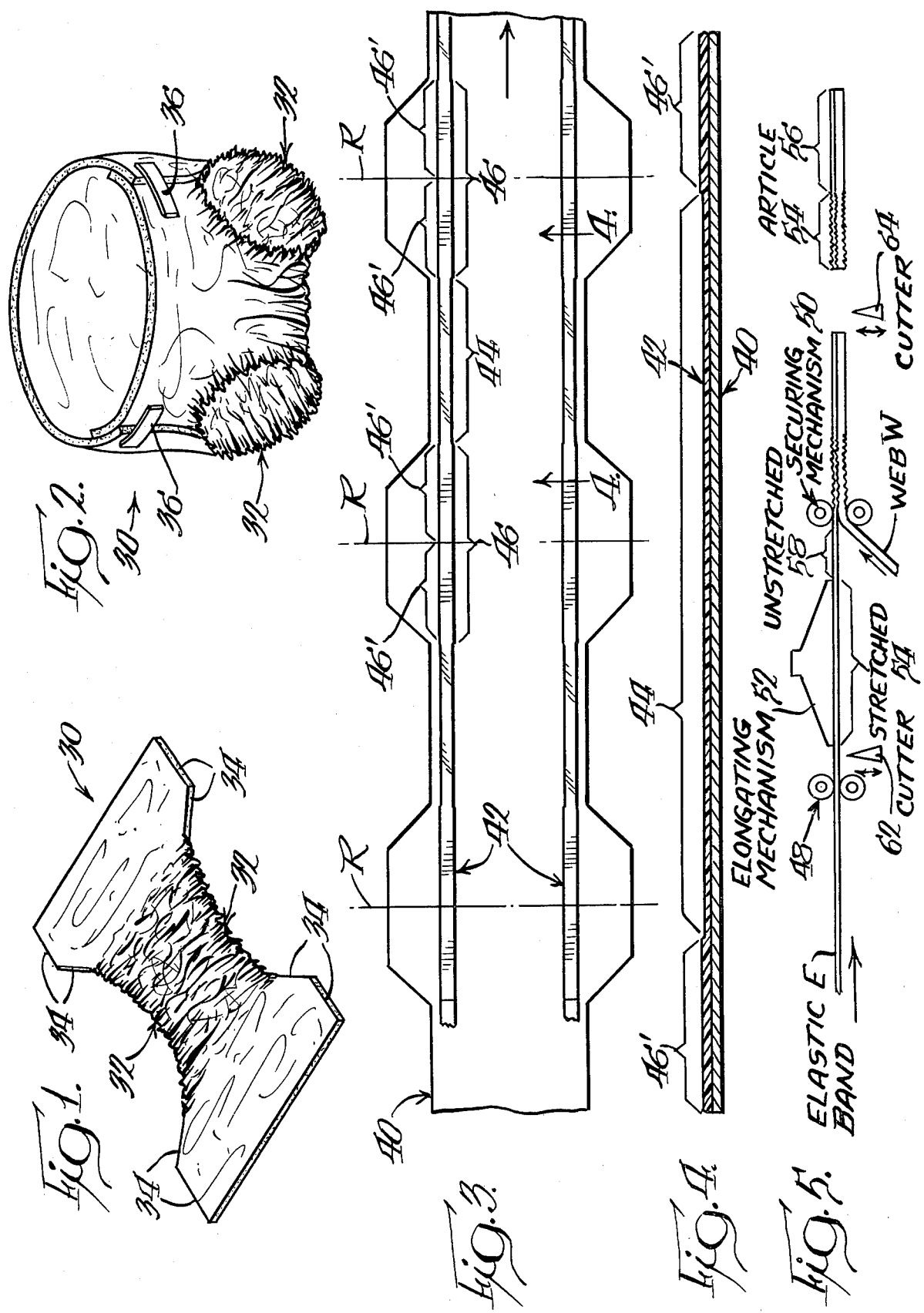

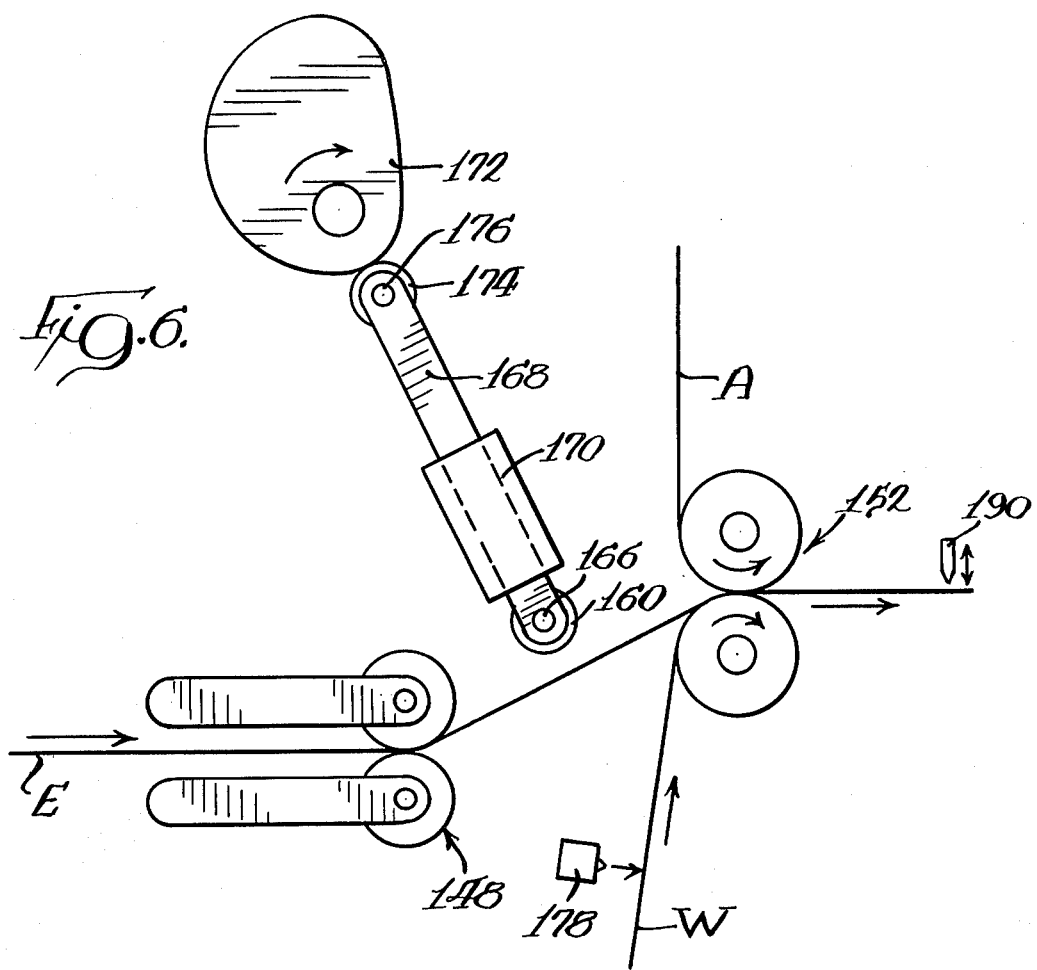
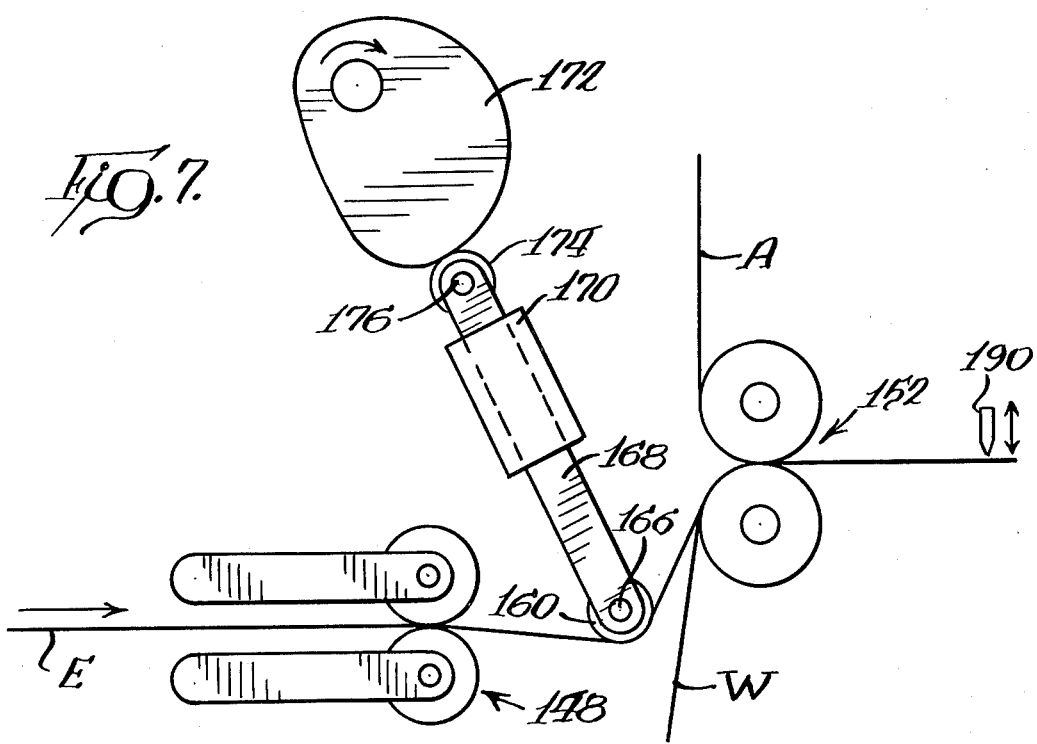

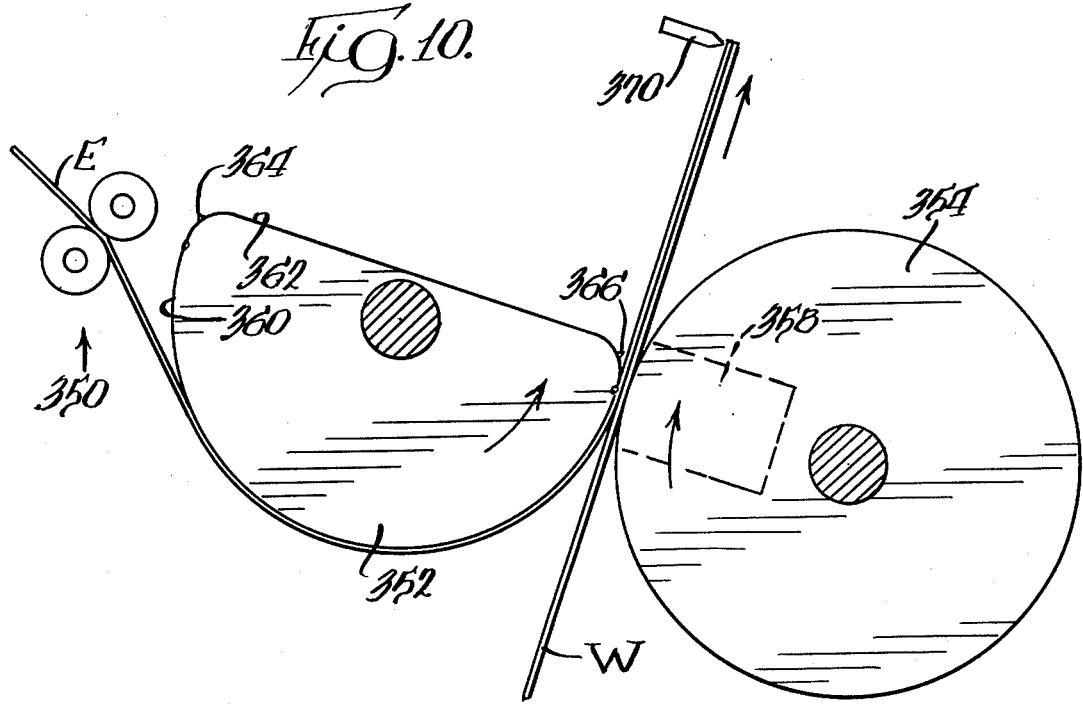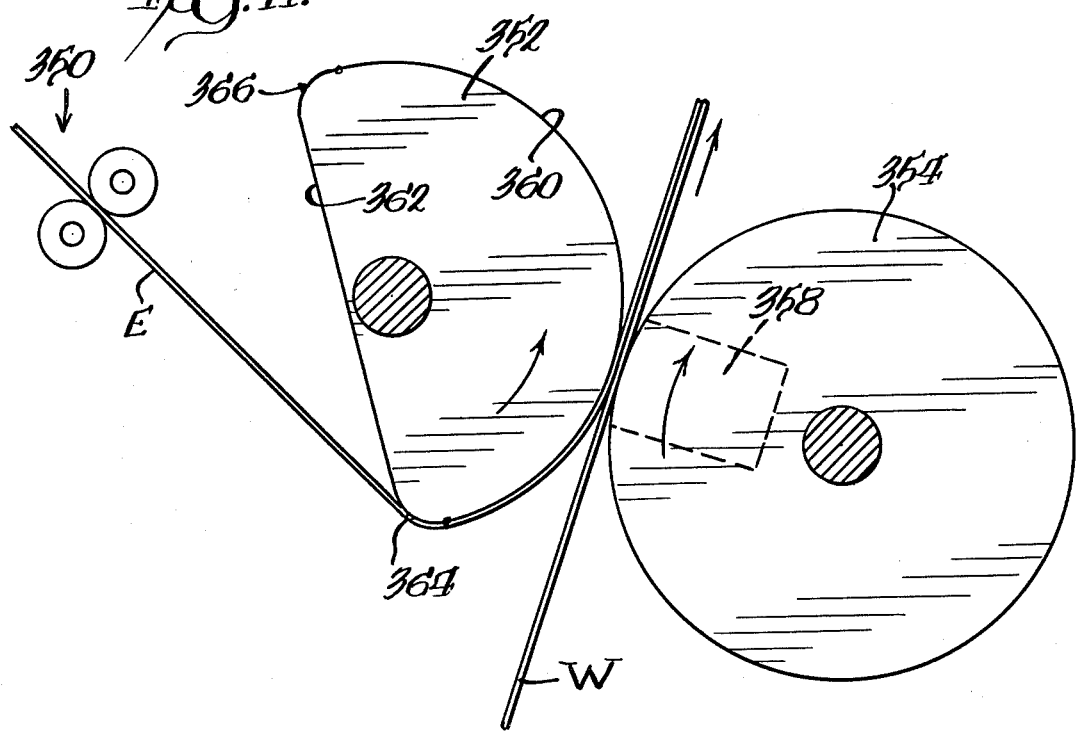

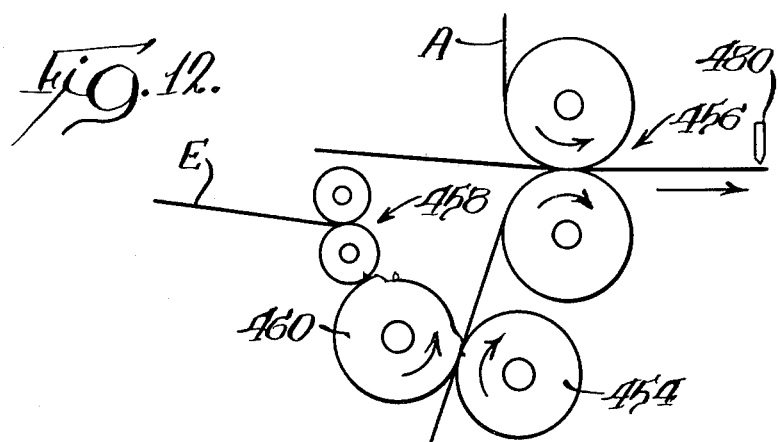
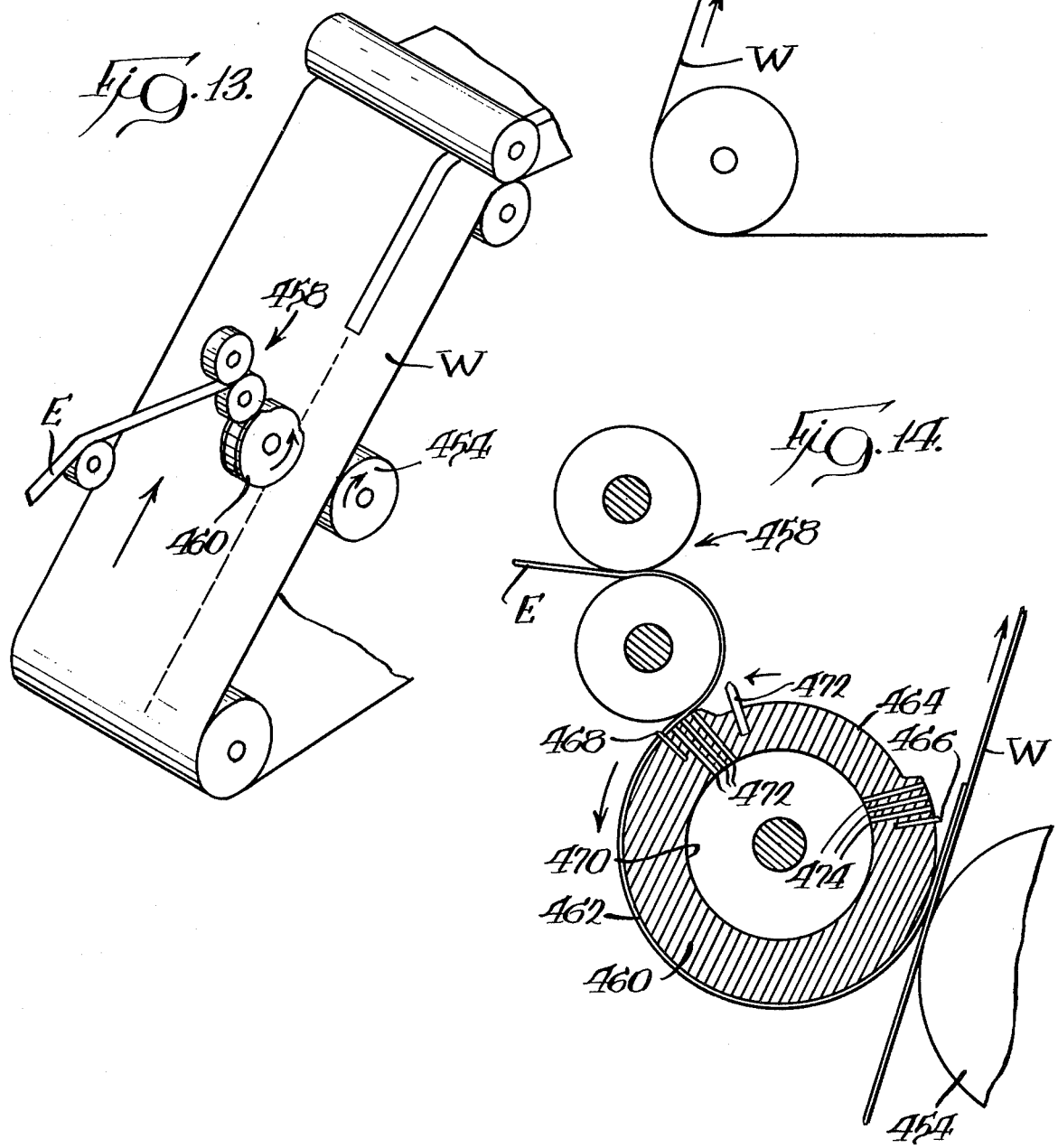
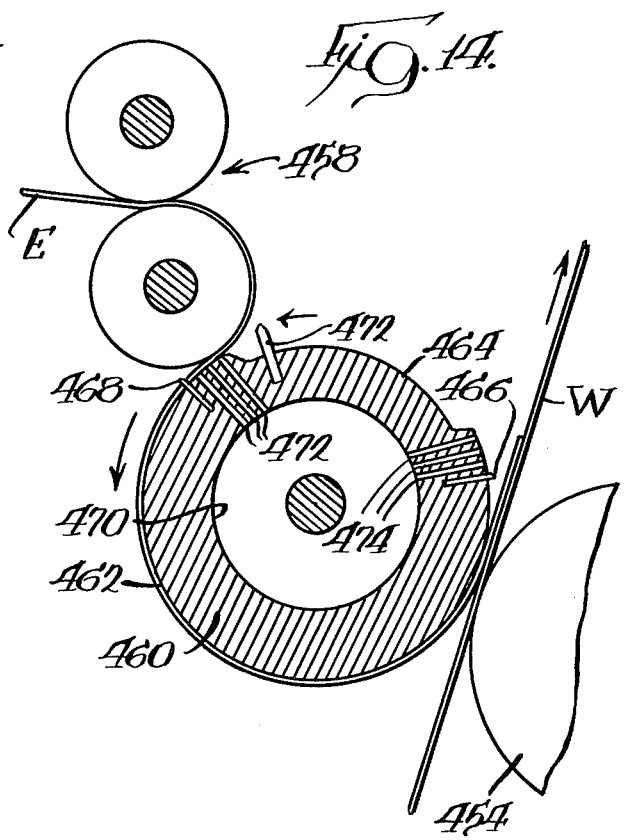

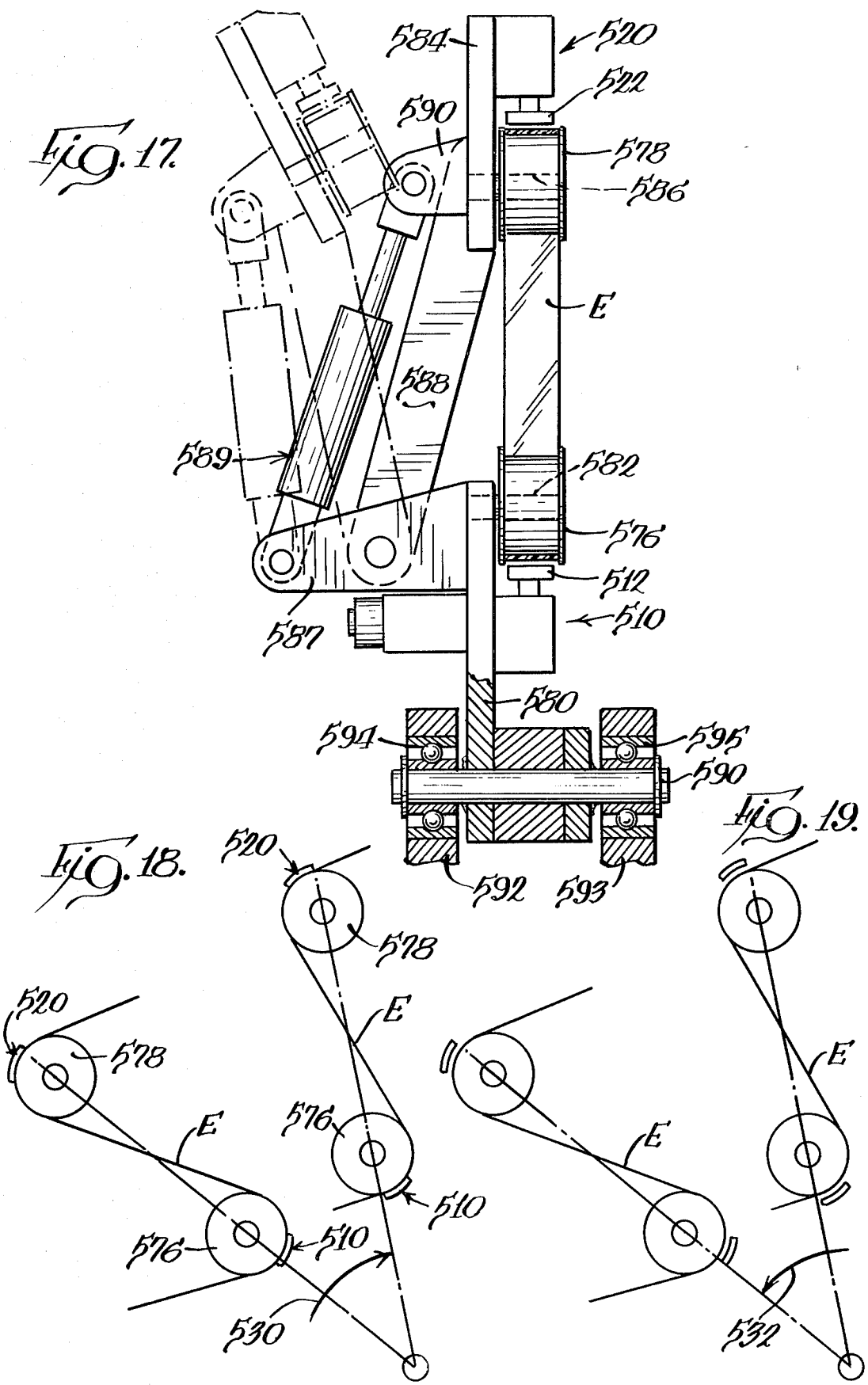

METHOD FOR EFFECTING SECUREMENT OF ALTERNATING STRETCHED AND UNSTRETCHED ELASTIC RIBBON TO A MOVING WEB

TECHNICAL FIELD

This invention relates to a method for the continuous or intermittent securing of a moving elastic member or band to a moving web or webs of disposable diaper components and the like, wherein at least one component is provided with an alternating sequence of stretchable or elastic portions and non-stretchable, inelastic portions along its length.

BACKGROUND OF THE INVENTION

Methods are known for fixing an elastic element or member, such as an elastomeric band or ribbon, to a flexible, substantially inelastic web of material defining clothing or components therefor, including briefs, panty briefs, disposable diapers, and the like.

Methods are known for applying an elastic element to a continuously moving web. The U.S. Pat. No. 3,828,367 to Bourgeois discloses a method for securing a stretched elastic element to a non-elastic fabric web and maintaining the assembled element on the web in a stretched condition until cut transversely of the direction of travel to produce separated panels. The apparatus is disclosed as including a rotating cylinder with a curved guide for imparting a non-linear configuration to the elastic element so that the ribbon follows a predetermined contour on the non-elastic fabric.

The U.S. Pat. No. 4,081,301 to Buell cites other prior art patents showing ways in which an elastic ribbon is joined to a moving web of material. The Buell patent itself discloses a method and apparatus for continuously attaching discrete lengths of elastic ribbon to a moving web in which the elastic ribbon is fed in a stretched condition to the web and in which the elastic ribbon is intermittently secured to predetermined regions of the web while so stretched. Subsequently, the web and elastic ribbon are transversely cut in an area where the elastic ribbon is not secured to the web, thereby forming severed, unadhered portions of elastic at both ends of each discrete length of stretched elastic ribbon adhered to the web and allowing the severed, unadhered ends of the elastic ribbon to relax and contract to their unstretched state.

With the method disclosed in the above-discussed Buell patent, it is important that (1) the moving elastic ribbon be secured to the moving web precisely at the predetermined regions on the web and (2) the moving elastic ribbon and moving web be severed precisely in the region where the elastic ribbon is not adhered to the web. For example, if the stretched elastic ribbon were accidentally adhered beyond the predetermined region and were then severed where it was accidentally adhered, the elastic ribbon would contract to impart an elasticized character beyond the desired predetermined region.

Thus, the securing mechanisms (such as adhesive applicators, heat sealing devices, etc.) must be carefully controlled and actuated to effect securement precisely in the desired regions. With very high speed manufacturing operations, accurate control of such mechanisms becomes difficult. Further, if the securing mechanism is a movable device, stresses imparted to the moving securing mechanism increase owing to the more rapid accelerations and decelerations which necessarily occur in high speed operations.

Also, the severing mechanism for cutting the web and elastic ribbon must be carefully controlled so that the elastic ribbon is cut in the unattached region. Obviously, at high speed manufacturing conditions, proper registration of a cutting mechanism becomes more difficult. If the cutting mechanism is a movable device, it must be designed to accommodate the higher stresses which result from the increased accelerations and decelerations.

In order to avoid the problems of precisely and accurately registering ribbon-securing and ribbon-severing mechanisms in high speed operations and in order to avoid the imposition of high stresses on such mechanisms subjected to rapid and intermittent movement, it would be desirable to provide a method and apparatus in which an elastic member could be secured to the moving web with stretched portions and unstretched or relaxed portions already formed in the elastic member before securement to the web.

With such a method, the securing means is preferably operated along the entire length of the elastic member so as to avoid the problems associated with high speed cyclical operation. Further, with this method, severing of the member in the relaxed segment would not cause the web to be further contracted. This would be true whether or not the relaxed segment of the elastic member was secured to the web.

SUMMARY OF THE INVENTION

According to the present invention, a method and apparatus is provided for securing an elastic member to a continuously moving, flexible, generally inelastic web of material, such as material defining disposable diaper components and the like, to impart a stretchable characteristic to predetermined portions of the components while preserving in other portions the generally inelastic character of the components.

A web of the components is moved along a path to a securement zone and an elastic member is continuously fed toward the securement zone and along a face of the web. Additional sheets of material, such as an absorbent pad and an overlying sheet, are also preferably fed to the securement zone. A portion of the member is elongated, upstream of the securement zone, to form a stretched segment adjacent an unstretched segment. The process of elongating the member is cyclically repeated as the member is fed so that an unstretched segment and a stretched segment of the member are alternately fed to the securement zone adjacent the web. The member may be severed upstream of the securement zone to provide a length defining at least a stretched segment therein, which stretched segment may be subsequently secured to the web (and preferably also to an overlying sheet) at a predetermined location. Alternatively, at least a stretched segment of the member may be first secured to the web and the member may then be subsequently severed, along with the web (and other overlying sheets as may have been applied), to create separate articles such as diapers.

In one embodiment of the method, the length of elastic member is formed as above with a stretched middle segment and relaxed end segments and the entire length of elastic member is then secured from end to end on a disposable diaper component with the entire stretched middle segment secured to a leg opening region of the diaper component. The length of the elastic member and components comprising an individual diaper is subsequently severed from the moving assembly. The stretched segment contracts to gather the material of the web to which it is secured for accommodating subsequent stretching of the leg opening region of the diaper. The unstretched end segments impart substantially no elastic or stretchable characteristic to the diaper on either side of the leg opening.

In one embodiment of the apparatus of the present invention, the continuous strip of the elastic member is fed between a pair of oppositely rotating rollers and extends therefrom to a second pair of rollers. Webs of material are fed through the second pair of rollers along with, and on either side of, the elastic member and at this location the elastic member is secured to the moving webs by suitable means, such as ultrasonic welding, application of adhesive, heat sealing, etc., at relatively closely spaced securement zones along the entire length of the webs. In this embodiment of the apparatus, the entire member is intermittently elongated upstream of the second set of rollers by contacting the elastic member between the first and second sets of rollers with an engaging member to move the elastic member out of its normal path and to thereby increase the linear travel distance of the elastic member between the two sets of rollers. After a suitable length of the stretched elastic member has been fed through the second set of rollers and secured to the webs, the engaging member is moved back to permit the elastic member to return to the original path between the first and second sets of rollers to form a relaxed or unstretched length. Repetition of this sequence provides alternating stretched and unstretched segments of the elastic member. The elastic member and the webs are severed at appropriate locations to separate individual articles, such as disposable diapers, downstream of the rollers.

According to the present invention, a contoured configuration can be given to the elastic member secured to the web. To this end, at least a portion of the elastic member is moved generally transversely of its length to give the transversely moved portion a non-linear shape as it is being secured to the web or webs. In this manner, the elastic member can be secured generally along the contour of a curved leg opening in a disposable diaper.

Thus it is seen that the present invention yields desirable and beneficial results—results which are not only new and different but which also provide a substantial improvement over the prior art.

Numerous other advantages and features of the present invention will become readily apparent from the following detailed description of the invention and of various embodiments thereof, from the claims and from the accompanying drawings.

BRIEF DESCRIPTION OF THE DRAWINGS

In the accompanying drawings forming part of the specification and in which like numerals are employed to designate like parts throughout the same, FIG. 1 is a perspective view of an unfolded disposable diaper formed in accordance with the invention;

FIG. 2 is a perspective view of the diaper illustrated in FIG. 1 shown in a orientation that would be assumed when properly placed about the body of an infant and conforming thereto;

FIG. 3 is a plan view of a moisture repellant backing sheet or web for forming interconnected disposable diapers with the absorbent pads and facing material removed to more clearly illustrate the pair of continuous elastic members adhered to the backing web (maintained under tension) in accordance with the invention;

FIG. 4 is a greatly enlarged fragmentary cross-sectional view taken generally along the plane 4—4 in FIG. 3;

FIG. 5 is a simplified, diagrammatic illustration of the method according to the invention;

FIGS. 6 and 7 are simplified diagrammatic illustrations of a first embodiment of the apparatus for effecting a first form of the method of the invention;

FIGS. 10 and 11 are simplified diagrammatic illustrations of a third embodiment of the apparatus of the invention for effecting a third form of the method of the invention;

FIGS. 12, 13, and 14 are simplified diagrammatic illustrations of a fourth embodiment of the apparatus of the invention for effecting a fourth form of the method of the invention;

FIGS. 16–19 are simplified diagrammatic illustrations of a fifth embodiment of the apparatus of the present invention for effecting the fifth form of the method of the invention.

DESCRIPTION OF THE PREFERRED EMBODIMENT

Figure 8:
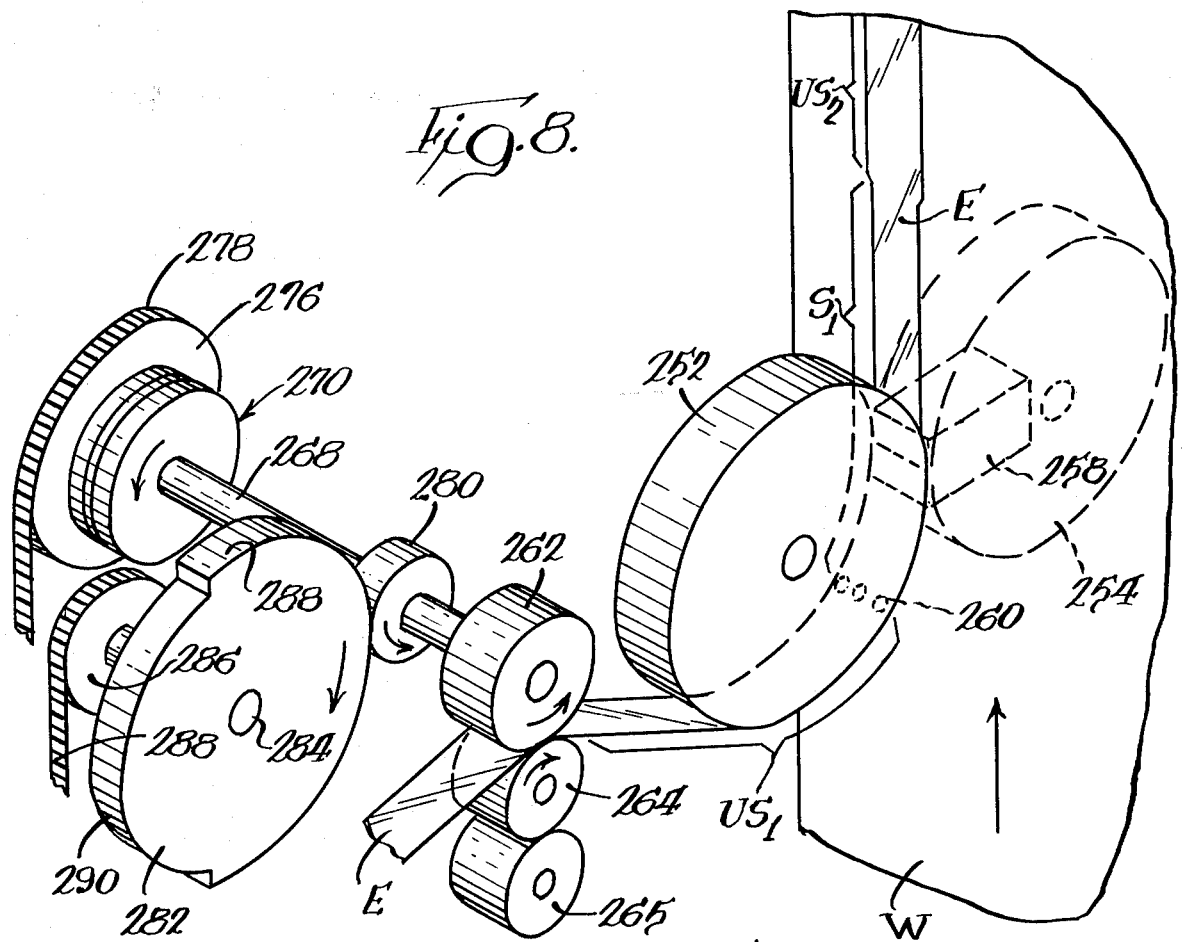
FIGS. 8 and 9 are simplified diagrammatic illustrations of a second embodiment of the apparatus of the invention for effecting a second form of the method of the invention.

The method and apparatus of the present invention may be used in many different forms. While the invention is susceptible of the embodiment in many different forms, there are shown in the drawings and will herein be described in detail preferred embodiments of the invention. It should be understood, however, that the present disclosure is to be considered as an exemplification of the principles of the invention and is not intended to limit the invention to the embodiments illustrated.

The precise shapes and sizes of the components for the embodiments of the apparatus herein described are not essential to the invention unless otherwise indicated. For ease of description, the various embodiments of the apparatus of this invention will be described in a normal operating position and terms such as lower, upper, horizontal, etc., will be used with reference to this normal operating positon. It will be understood, however, that the apparatus of this invention may be manufactured, stored, transported and sold in an orientation other than the normal operating position described.

The various embodiments of the apparatus of the invention have certain conventional drive mechanisms and control mechanisms, the details of which, though not fully illustrated or described, will be apparent to those having skill in the art and an understanding of the necessary functions of such machanisms.

Referring now to the drawings, FIG. 1 shows a disposable diaper 30, which is fabricated from flexible materials and which incorporates elasticized areas 32 which partially define leg openings between non-elasticized longitudinal edge regions 34. As illustrated in FIG. 2, when the disposable diaper 30 is placed properly about an infant, the elasticized regions 32 form a generally circular configuration about the infant's legs and, owing to the elasticity thereof, are constricted about the infant's legs to follow the specific contours of the infant's legs. The non-elasticized regions 34 extend upwardly from the infant's legs along the infant's sides and are overlapped as necessary to insure a proper fit about the infant. The diaper may be secured on each side with suitable fastening means such as strips of tape 36.

The diaper 30 may be comprised of a plurality of layers of material, such as (1) a water-impervious or water repellent sheet, (2) a water-absorbent fibrous pad, but smaller than the repellent sheet and centrally disposed thereon, and (3) an overlying facing layer of material, which is equal in dimension and coterminous with the repellent sheet and in contact therewith and secured thereto in the marginal portions of the diaper extending peripherally beyond the absorbent pad. Such a multi-layered construction, and the materials therefor, are fully described in the U.S. Pat. No. 3,612,055 to Mesek et al., which, to the extent it is consistent herewith, is incorporated herein by reference.

FIG. 3 shows a partially completed structure from which a plurality of interconnected diapers are formed on a production line. Specifically, a repellent sheet or moisture-impervious backing web 40 is shown as having, between each pair of reference lines R, a cutout leg opening configuration substantially of the same planar shape as that of the diaper 30 illustrated in FIG. 1. Reference lines R are shown merely to illustrate the ends of each inter-connected diaper. The cutout configuration of the web 40 may be produced by well-known conventional methods which form no part of the present invention.

Secured to the backing sheet 40 are a pair of spaced apart, parallel elastic memebrs 42. For purposes of illustration, the absorbent pad and facing layer, which would normally overlie the backing web 40, are not shown. Typically, although not necessarily, the facing layer, extending beyond the absorbent pad and in registry with the web 40, would also be secured to the elastic members 42. The backing sheet 40 is preferably also coated with lines or bands of hot melt adhesive (not shown) in an orientation parallel to the elastic members 42 for securing the facing layer and absorbent pad to the backing sheet 40.

The elastic member 42 may be a sheet, film, apertured member, filaments or a plurality thereof, ribbon or the like which is easily stretched by hand and, when stretched to less than its yield point, can recover upon release to approximately its original unstretched length or to some other length sufficiently shorter than stretched length to function satisfactorily in the disposable diaper. Preferably, the elastic member is made from elastomeric materials such as rubber or suitable types of thermoplastic film.

The elastic member 42 need not be directly secured to the other diaper components. A reticulated film may be used for member 42 and may have a plurality of spaced apertures along its length and through which apertures the backing web and facing sheet may be secured by suitable means, such as spots of adhesive.

As illustrated in FIG. 3, the elastic member 42 extends continuously along the web 40 in alternate stretched segments or portions 44 and unstretched or relaxed segments or portions 46. When an individual diaper is severed from the continuous array, along the reference lines R, the individual diaper is seen to have a length of elastic member extending from end to end with a stretched midportion 44 and relaxed end portions 46'.

According to the method of the present invention, the stretched segment or portion 44 is secured, adhered or otherwise fixed to the web 40 (and to an overlying facing sheet). The unstretched or relaxed end portions 46' are preferably also fixed to the web 40 (and to the overlying facing sheet). However, the method of the present invention contemplates that the relaxed end portions 46' may be left unadhered on the surface of the web 40 if desired. In such a case, an overlying facing layer is preferably secured to the backing web 40, as with lines of hot melt adhesive, on either side of the elastic member 42 so as to retain the relaxed portions 46' between the facing material and backing web 40. Alternatively, the elastic member may also be applied to the side of a diaper component or web that will comprise the exterior surface of the finished diaper.

In any case, since the relaxed end portions 46' are not laid on the backing web 40 in a stretched condition, the relaxed end portions 46' can impart no elastic character to the underlying portion of the backing web 40. Of course, if the relaxed end portions 46' are secured along their length to the backing web 40, they can impart substantially no elastic character to the backing web 40 because (1) the relaxed portions 46', being unstretched, are in their natural state and cannot contract to pull the backing web together and (2) the relaxed end portions 46' cannot be stretched from their relaxed condition because they are secured to the backing web 40 which is substantially inelastic and permits no stretching.

There are advantages to securing the relaxed end portions 46' to the backing web 40 along with the stretched portions 44. Specifically, if the elastic member 42 is applied to the side of a diaper component that will comprise the exterior surface of the finished diaper, securement of the end portions 46' causes them to be held down against the component and prevents them from otherwise being accidentally engaged or caught during subsequent manufacturing operations. In those articles where at least one side of the elastic member 42 would always be exposed, securement of the relaxed end portions 46' would obviously be desirable to prevent accidental snagging of those portions during use. Further, with the type of disposable diaper 30 illustrated in FIGS. 1 and 2, securement of the relaxed end portions provides an additional reinforcing effect under the fastening tapes 36. This increases resistance to accidental pull-out of the tape from the diaper.

In addition, securement of the entire elastic member 42 (by means of an array of closely spaced securement zones or otherwise), including the relaxed end portions 46', has another advantage compared to those methods which employ movable mechanisms to secure only the stretched portions 46' to the web 40. Such securing mechanisms could include stitching devices, heat sealing devices, and adhesive applicators, etc. When many of such devices are operated on a intermittent basis at extremely high production line speeds, accurate registration of the devices with just the stretched portions 46' on the backing web 40 becomes difficult. Further, the necessary cyclic operation at extremely high speeds could result in relatively large forces owing to the high accelerations and decelerations of those mechanisms that undergo cyclic movement to effect the securement of just the stretched segments 46'.

FIG. 5 illustrates, by means of a very simplified diagram, the basic method of the present invention. In particular, a web W is fed through a securing station or mechanism 50 at a predetermined linear speed. The elastic member or band E is also fed to the securing station 50 adjacent the web W. A suitable mechanism, such as a pair of coacting drive rollers 48 may be employed as necessary to feed the member E.

Although only one member E is illustrated in FIG. 5, it is to be understood that a plurality of such elastic members may be similarly fed in parallel fashion and operated upon as will be described in detail hereinafter for one such member. Similarly, specific embodiments of the apparatus for effecting the method of the present invention will be described hereinafter with respect to the securement of a single elastic member or band and it is to be understood that two or more elastic bands may be secured by such apparatus simultaneously operating upon the bands in parallel alignment.

With continued reference to FIG. 5, the strip of elastic band E is elongated by a mechanism 52, upstream of the securing mechanism 50, to form at least one stretched portion or segment 54 adjacent one relaxed or unstretched portion or segment 56. The elongated mechanism 52 may take a variety of forms and may move with the band E or rotate against the band E. The specific embodiments of the elongating mechanism 52 will be described hereinafter.

The stretched and unstretched segments 54 and 56, respectively, may have relative lengths as desired and the stretched portion may be longer than the unstretched portion, as shown, or vice versa. In any case, the method of the present invention provides, by means of the elongating mechanism 52, an alternating sequence of stretched and unstretched segments in band E as the band runs through the securing mechanism 50 adjacent the web W.

As illustrated in FIG. 5, a length of the band E, containing at least one stretched segment 54, may be severed upstream of the elongating mechanism by means of a cutter 62. Alternatively, or in addition, a cutter 64 may be provided downstream of the securing mechanism 50 to sever the individual articles and, if necessary, to sever the band E.

Although FIG. 5 illustrates the formed article with the band having one unstretched portion 56 and one stretched portion 54 imparting an elasticized character to a portion of the article, it is to be realized that a number of alternating stretched and relaxed segments can be applied to a single article.

Typically, with the disposable diaper of the type illustrated in FIGS. 1 and 2 and discussed above, the elastic band E is applied to the web so that the article has an elasticized midportion and two relaxed end portions.

Of course, if a disposable diaper were being fabricated according to the method of the invention as illustrated in FIG. 5, the web W would be a water repellent backing sheet and an absorbent pad and facing layer would be applied on top of the web W. The pad and facing layer would be typically secured to the web W by suitable means, such as lines of hot melt adhesive or the like, so as to sandwich the band between the backing web and the facing layer exterior of the lateral edge of the absorbent pad. The absorbent pad and facing layer are not illustrated in FIG. 5 but would typically enter the securing region or mechanism 50 on the side surface of the elastic band opposite from the web W.

Various embodiments of the elongating mechanism 52 will next be described along with various forms of the method of the present invention for applying an elastic member to a flexible web. In a first embodiment illustrated in FIGS. 6 and 7, an elastic member or band E is fed from between a pair of feeder rolls 148 through a predetermined path, in this case a generally straight line, to a pair of pinch rolls 152. The band E is typically fed under a small amount of tension but is not initially stretched or elongated any substantial amount as it is so fed in the straight line path. A web of material W, to which the elastic band E is to be secured, is fed by conventional means to pinch rolls 152. If desired, one or more additional components (e.g., an absorbent pad and facing layer) may be fed to the pinch rolls 152 for securement to the backing web W and/or elastic band E, such as is illustrated for a strip of material A.

Discrete lengths of the elastic band E are controllably elongated to form a stretched segment by means of a moving dancer roll 160 as illustrated in FIG. 7. Specifically, dancer roll 160 is rotatably mounted about pin 166 to a reciprocative member 168 mounted within housing 170 carried on a suitable frame (not illustrated) and biased relative to housing 170 (by means not illustrated) against a rotating cam 172. For accommodating the rotation of cam 172, a cam follower in the form of a wheel 174 is mounted on shaft 176 to member 168. Rotation of the cam 172 causes the dancer roll 160 to engage the elastic band E and increase the linear travel distance of the band between the feed rolls 148 and the pinch rolls 152 as illustrated in FIG. 7.

The stretched segment formed by this elongation travels through the pinch rolls 152 where the band may be secured continuously, or intermittently, to the web W alone, or to both web W and strip A. In the embodiment illustrated in FIG. 6, the web W is preferably sprayed along its length with discrete bursts of an adhesive from sprayer 178 to create discrete, but closely spaced, securement zones, so that when the elastic band E is forced against the web W by the pinch rolls 152, the elastic band E becomes secured to the web W. Thus, as the stretched segment of the elastic band formed in FIG. 7 travels through the pinch rolls 152, it will be adhered in the stretched condition to the web W. Securement of strip A to band E may be effected by similar means or by other means (not illustrated).

Continued rotation of the cam 172 permits the dancer roll 160 to be moved, by the biasing means in housing 170, to the position illustrated in FIG. 6 out of engagement with the elastic band E. At this point, the elastic band is relaxed and an unstretched segment passes through the pinch rolls 152 and is secured in the same manner to web W as the stretched segment. Thus, it is seen that with each complete rotation of cam 172, a stretched segment and an unstretched segment of band E are formed and secured to the web W.

Downstream of rolls 152, the assembled band and webs W and A may be severed as necessary by a suitable cutter means 190 to separate the individual articles.

Although the elastic band E is illustrated in FIGS. 6 and 7 as being secured by means of adhesive to the web W, it is to be realized that any suitable securement means may be employed that is compatible with the materials, including gluing, stitching, ultrasonic welding, heat sealing, etc. Further, it is to be understood that the securing of the elastic band E to the web W may be performed on an intermittent basis and in a manner that leaves relatively long portions, say each unstretched segment, unsecured. However, the stretched segment would typically be secured throughout its stretched length to the web W by means of closely spaced securement zones (e.g., spaced apart drops of adhesive) to provide a uniform elasticized character to the web W. The small unsecured region of web W between any two adjacent securement zones would buckle (upon relaxation of the elastic member) to provide a desired gathering or bunching of the material. The relaxed segment would also typically be secured throughout its length by means of closely spaced securement zones, though failure to secure the relaxed segment will not affect the inelastic character of the adjacent region of the web.

Figure 9:
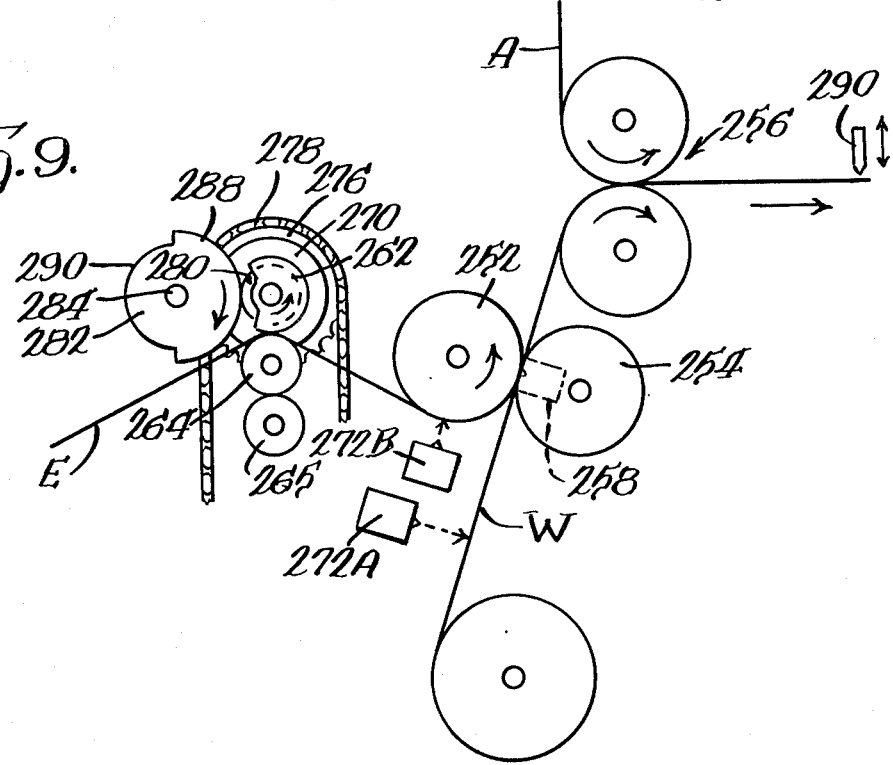

The second embodiment of the apparatus of the present invention for effecting a second form of the method of the present invention is illustrated in FIGS. 8 and 9. Specifically, as in the first embodiment described above, FIG. 9 illustrates an elastic member or band E fed to a securement zone, such as may be defined between an anvil roll 252 and roll 254 along with the web W. Downstream of roll 254 the elastic band E and web W may be combined with one or more additional layers A, as by securing web W and a layer A together at a pair of laminating rolls 256. Again, lines of hot melt adhesive (not illustrated) may be applied to web W for this purpose.

The elastic band E is secured to web W at roll 252. Depending upon the composition of the elastic band E, adhesive may be applied to the band from nozzle 272B or adhesive may be applied to the web W by nozzle 272A. Preferably, as explained with reference to the first embodiment illustrated in FIGS. 6 and 7, the adhesive is applied along the entire length of band but in discrete, closely spaced quantities. If a heat sealable elasticizable thermoplastic film is used for the elastic band E, the backup roll 254 may be replaced by an ultrasonic welding burn 258 (hidden behind the web W and shown in dashed lines in FIG. 8). The welding horn would preferably be operated to produce discrete, but closely spaced securement zones. Regardless of the nature of the securement of the elastic band E to the web W, the elastic band E is fed into contact with the web W in alternating stretched and unstretched segments as will next be explained.

With reference to FIG. 8, the anvil roll 252 is provided with means for gripping the elastic member or band E, such as gripping pins or a saw tooth region 260. The anvil 252 is rotated at a constant speed, by conventional means not illustrated, to drive the elastic band and web at line speed so as to match the feed speed of the layer A.

Upstream of the anvil roll 252 the elastic band E is driven by a variable speed feed roll 262 in cooperation with a suitable backup or idler roll 264. An additional roll 265 may be provided to be rotated by, and against, idler roll 264. Feed roll 262 is mounted on axle 268 which in turn is driven through a conventional slip clutch 270 by a sprocket 276 which is rotated by conventional drive means (not illustrated) through drive chain or belt 278. Drive shaft 268 also carries a friction roll 280 which is fixed for rotation with shaft 268 and is adapted to engage a specially shaped overdrive wheel 282 fixedly mounted on shaft 284 which is in turn driven through sprocket 286 by a conventional drive means (not illustrated) through a drive chain or belt 287.

The overdrive wheel 282 has an increased radius portion defining a partial circumferential drive surface 288 which is adapted to engage the friction roll 280. A reduced radius portion of the overdrive wheel 282, defined by a partial circumferential surface 290, does not come into contact with the friction roll 280 during rotation of the over-drive wheel 282.

The slip clutch 270 is adapted to permit the shaft 268 and friction roll 280 to be rotated at a greater angular velocity than the drive sprocket 276 whenever the friction roll 280 is engaged by the drive surface 288 of the overdrive wheel 282. On the other hand, during each portion of the rotation of overdrive wheel 282 when its drive surface 288 is not in contact with the friction roll 280, the friction roll 280 and feed roll 262 are driven at a constant angular velocity by the drive sprocket 276 acting through clutch 270. When the feed roll 262 is drive through the clutch 270, its peripheral speed is less than the peripheral speed of the anvil roll 252. This causes the elastic band E to be elongated and form a stretched segment. As the stretched segment of the elastic band E is carried past the backup roll 254 or ultrasonic welding horn 258, it is secured to the web W.

By synchronizing the rotation of the anvil roll 252 with the overdrive wheel 282, the anvil roll 252 can be rotated to bring the gripping teeth 260 into engagement with the stretched elastic band E just when the friction roll 280 starts to be rotated at the increased angular velocity through overdrive wheel 282.

The increased angular velocity of roll 280 speeds up the feeding of the elastic band E by an amount sufficient to relax the segment of band between the feed roll 262 and gripped region of band on anvil roll 252. The relaxed or unstretched segment is then continued to be fed by anvil roll 252 onto the web W and the unstretched segment may, if desired, be secured to the web W in the same manner as the stretched segment.

When the overdrive wheel 282 rotates to the point at which it no longer engages roll 280, the feed roll 262 is again driven at reduced angular velocity through clutch 270. This causes the band to elongate between the securement region (roll 254 or ultrasonic horn 258) and roll 262 to form another stretched segment.

In FIG. 8, the unstretched segment $US_1$ is shown being formed around the anvil roll 252 with a stretched segment $S_1$ shown being secured to web W at anvil roll 254 and with an unstretched segment $US_2$ shown secured to web W beyond segment $S_1$.

The web and elastic band (and other sheets or webs as may have been assembled) may be severed downstream of rolls 256 by a suitable cutter means 290A (FIG. 9) to separate individual articles.

The third embodiment of the apparatus of the present invention for effecting a third form of the method of the present invention is illustrated in FIGS. 10 and 11. Specifically, the elastic member or band E is fed from a pair of feed rolls 350 around a generally semi-cylindrical anvil 352 and between an adjacent backup roll 354 or ultrasonic welding horn 358 (shown in dashed lines). Also fed along with the elastic band E is the web W. Additional sheets or webs (not illustrated) may be fed downstream in a manner similar to that shown in the second embodiment (FIG. 9) for sheet A.

The anvil 352 has a band stretching first surface 360 and a band relaxing second surface 362. At the junction of the first and second surfaces, on each side of the anvil roll 352, saw tooth grippers 364 and 366 are provided. For purposes of explanation hereinafter, gripper 366 may be regarded as "leading" the "trailing" gripper 364 for the counterclockwise rotation illustrated in FIG. 10.

In operation, the elastic band E is fed from an orientation, relative to the rotating anvil 352, which causes the elastic band to be stretched and elongated about the first band stretching surface 360 during a portion of the rotation of the anvil 352. When the leading saw tooth gripper 366 contacts the elastic band E, it holds the elastic band E in that region against movement relative to the first band stretching surface 360. As the leading saw tooth gripper 366 is rotated to bring the stretched band E into contact with the web W as illustrated in FIG. 10, the band and web are secured by any of the means previously discussed with reference to the first and second embodiments illustrated in FIGS. 6–9.

Continued rotation of the anvil 352 brings the trailing saw tooth gripper 364 into engagement with the band E as illustrated in FIG. 11. The band relaxing second surface 362 of anvil 352 rotates toward the band E. Owing to the orientation of the feeding of band E from rolls 350 relative to the anvil 352, the stretched band relaxes against the surface 362.

Surface 362 is shown as a generally planar surface having a band contacting length much shorter than the band contacting length of the semi-cylindrical band stretching surface 360. Consequently, the elastic band E, no longer being forced into the elongated condition, relaxes to form an unstretched segment. Continued rotation of the anvil 352 brings the leading saw tooth gripper 366 back into engagement with the elastic band E and this defines the upstream end of the relaxed segment, which relaxed segment is rotated adjacent the web W between the leading and trailing saw tooth grippers 366 and 364, respectively.

Since the relaxing surface 362 and unstretched segment of band E thereon will not be in contact with the backup roll 354, if one is used, or with the ultrasonic horn 358, if one is used, securement of the unstretched segment by such means must be performed further downstream where the unstretched segment of elastic band E and web W can be forced in surface-to-surface contact. Of course, in some applications it may be desired to leave the relaxed segments unsecured.

The assembled web and elastic band may be severed into individual articles downstream of anvil 352 by a suitable cutter means 370 (FIG. 10).

If desired, variations in the amount of relaxation and elongation in the segments of elastic band E can be effected by driving the anvil member 352 with a suitable variable angular velocity, such as may be effected through the clutch and overdrive mechanisms illustrated and described above with reference to the second embodiment illustrated in FIGS. 8 and 9.

A fourth embodiment of the apparatus of the present invention for effecting a fourth form of the method of the present invention is illustrated in FIGS. 12–14. In FIG. 12, a sheet A is shown fed from above to a pair of rolls 456. The web W is fed upwardly past a back up roll 454 to rolls 456. The elastic member or band E is threaded through a pair of constant speed feed rolls 458 and around a rotating stretching member or roll 460.

As shown in greater detail in FIG. 14, the stretching roll 460 has a peripheral engaging surface 462 and a reduced radius relaxed band carrying surface 464. A gripping means such as leading gripping pins 466 and trailing gripping pins 468 project outwardly from the circumference of the engaging surface 462 of the stretching member 460. The stretching member 460 preferably has an internal vacuum chamber 470 and a plurality of vacuum bores 472 communicating between the vacuum chamber 470 and the engaging surface 462 adjacent pins 468. Similarly, vacuum bores 474 communicate between the vacuum chamber 470 and the surface 462 adjacent leading gripper pins 466.

In operation, the stretching member 460 is rotated at a speed sufficient to stretch a segment of the elastic band E around the engaging surface 462 when it is gripped by the leading gripper pins 466. Continued rotation of the member 460 brings the stretched segment into contact with the back up roll 454 where it may be secured to the web W by suitable means (not illustrated), such as ultrasonic welding or with adhesive, as previously described. Continued rotation of the stretching member 460 causes the trailing gripper pins 468 to engage the elastic band E. Further rotation of the stretching member 460 brings a suitable severing device, such as a knife blade 471 mounted to roll 460, into contact with the elastic band E against one of the feed rolls 458 so that the elastic band is severed. Continued rotation of member 460 carries the severed band end portion to the back up roll 454 for placement on web W where, if desired, it may be secured also.

When the knife 471 severs the stretched elastic band E, the elastic band on each side of the knife 471 snaps away from the knife. One portion relaxes forwardly and against the vacuum bores 472. The other portion relaxes against the rolls 458 and continues to be fed towards the relaxed band retaining surface 464. This portion of the band is fed against the surface 464 into the circumferential space defined by the reduced radius of the stretcher roll 460. Eventually the vacuum bores 474 come into contact with a portion of the severed elastic band E so that the portion is maintained on the stretcher roll 460 as it continues to be rotated toward back up roll 454.

Further rotation of the stretching member 460 causes the leading gripper pins 466 to engage a region of the band and to then begin stretching the band E about the stretching surface 462. The unstretched or relaxed segment of band lying on the surface 464 and held by vacuum against the vacuum bores 474 is carried in the relaxed condition past the back up roll 454.

As the stretched segment of elastic band E is secured to the web W, it pulls the leading relaxed segment away from the reduced radius surface 464 and from vacuum bores 474. The relaxed segment may be left unsecured or may be secured to the web at a subsequent downstream station.

With this embodiment, severed lengths of elastic band are provided—each length having a stretched midportion and relaxed end portions. The web W may be subsequently severed downstream of rolls 456 by a suitable cutter 480.

Figure 15:
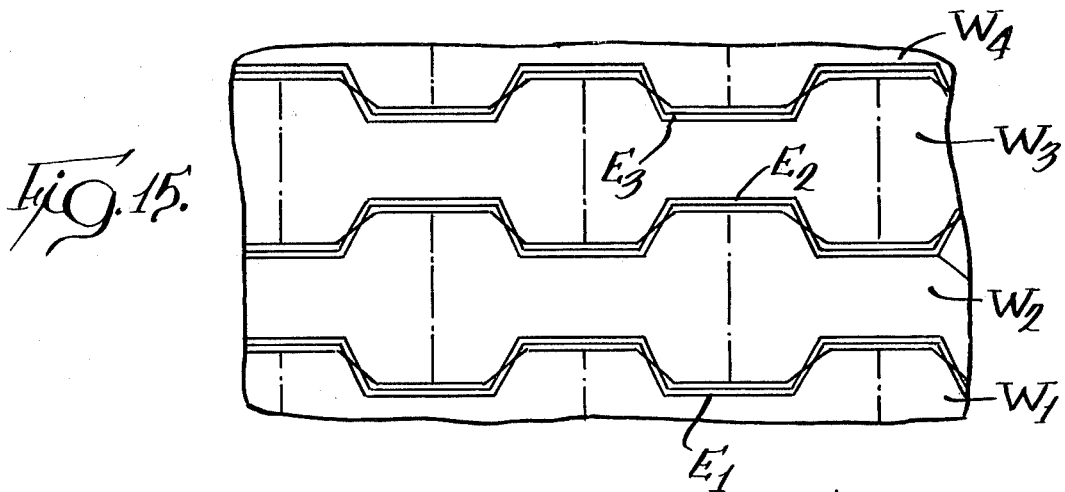
FIG. 15 is a plan view of a plurality of parallel backing webs, similar to the backing webs illustrated in FIG. 3 and which may be defined on a single wide sheet, but showing the elastic members secured in a non-linear configuration in accordance with a fifth form of the method of the present invention.
Figure 16:
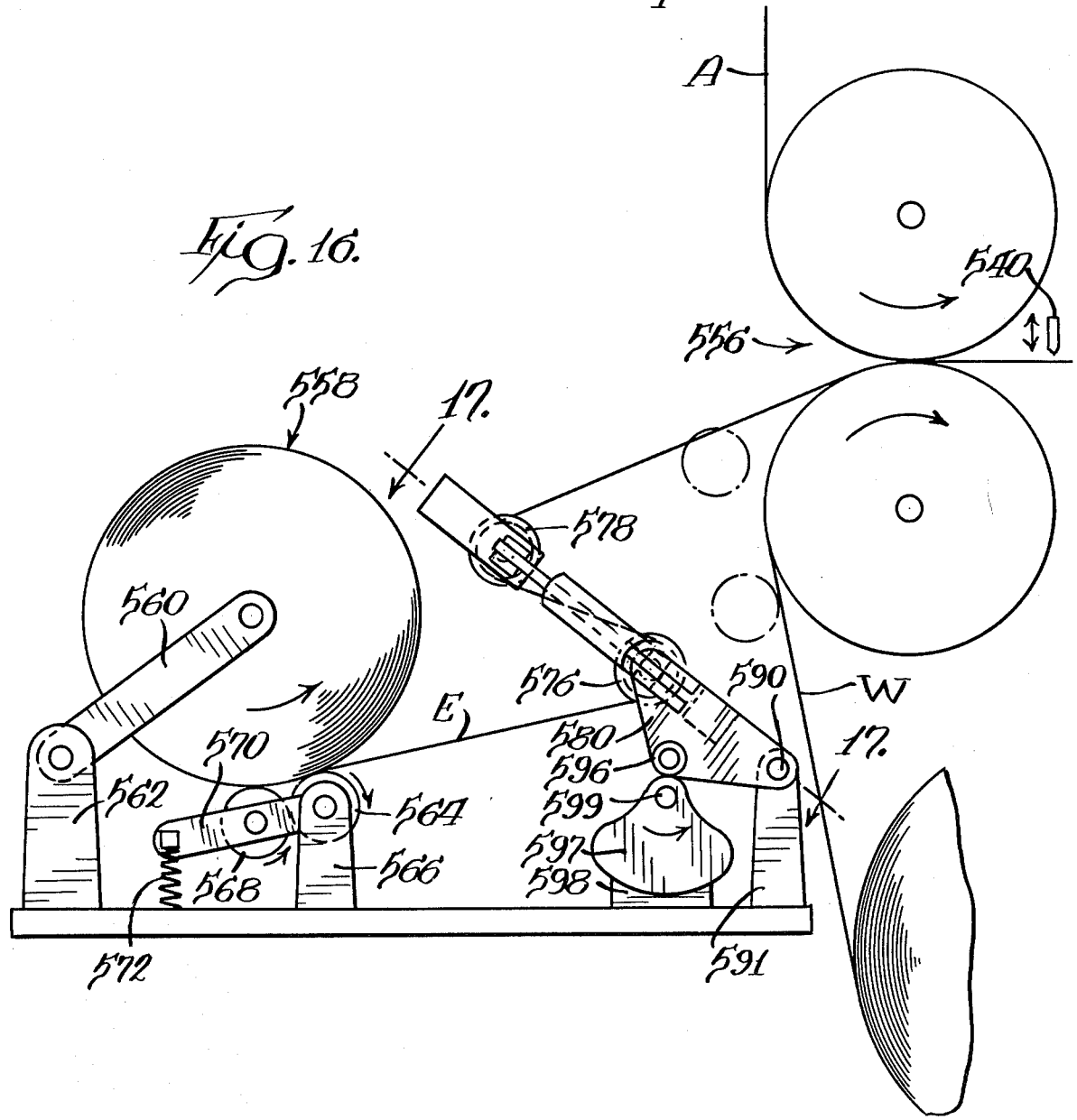

A fifth embodiment of the apparatus of the present invention for effecting a fifth form of the method of the present invention is illustrated in FIGS. 16, 17, and 18. The apparatus operates to apply alternately stretched and unstretched segments of an elastic member or band to a moving web wherein portions of the band are moved generally transversely of the band length to give a non-linear shape to the band as it is attached to the web. The configuration of the secured band to the web is illustrated diagrammatically in FIG. 15 for a plurality of moving webs $W_1$, $W_2$, $W_3$, and $W_4$. The webs may be defined in one single wide sheet or may be separate sheets aligned in parallel. Webs $W_1$, $W_2$, $W_3$, and $W_4$ have lateral boundaries or edges in the configuration of a typical contoured diaper and elastic bands $E_1$, $E_2$, and $E_3$ are shown adhered to the webs, along their edges or boundaries, in a non-linear manner generally corresponding to the diaper edges. However, as can be seen from studying FIG. 15, the diapers defined on each web of material are arranged so that a diaper on one web is positioned one-half of a diaper length forward or rearward of the adjacent diaper lengths on either side. In this manner, the lateral edge of the leg opening of one diaper also simultaneously defines the lateral edge of the body portions of adjacent diapers. The band is secured in a non linear fashion to lie along the leg opening region of one diaper and then crosses over to the adjacent diaper and lies along the leg opening of that diaper.

Such a contoured elastic band configuration can be produced with the apparatus shown in side view in FIG. 16. A web W, which may be comprised of a plurality of adjacent webs, such as webs $W_1$, $W_2$, $W_3$, and $W_4$, illustrated in FIG. 15, passes upwardly to and between a pair of driving pinch rolls 556. Additional layers, such as layer A, may be fed from above between pinch rolls 556 while the elastic band E is fed to the pinch rolls 556 between layer A and the web W.

The elastic band E may be wound about a spool 558 which is rotatably mounted to arm 560 which is in turn pivotally mounted to support member 562. A rotatably mounted driving roll 564 is mounted to a support 566 for engaging the outermost layer of band E on the roll 558. To prevent an overdrive condition, a friction brake mechanism may be employed, such as the brake roll 568 rotatably mounted to arm 570 which is in turn pivotally mounted at one end to support 566 and which is biased at the opposite end toward the roll 558 by suitable means, such as spring 572. The brake roll 566 is constantly engaged with the driving roll 564 and is thus rotated in the direction opposite from the roll 564. By appropriate adjustment of the spring 572, the brake roll 568 may be forced to a greater or lesser extent as desired, against the roll 558 to apply a constant resistance to the rotation of roll 558 and thus act to prevent a peripheral speed greater than the peripheral speed of the driving roll 564.

Downstream of the driving roll 564, the elastic band E is threaded partially around a first, lower stretch roll 576 in a first direction and partially around a second stretch roll 578 in a second direction. As best illustrated in FIGS. 17 and 18, the first stretch roll 576 is rotatably mounted to a rocker arm 580 about pin 582. The upper or second stretch roll 578 is mounted to an upper plate 584 by means of shaft 586 and the upper plate 584 is pivotally mounted to an extension 587 on the rocker arm 580 by means of link 588.

As best illustrated in FIG. 17, the upper plate 584 and second stretch roll 578 are movable between a first position illustrated in solid line and a second, moved position illustrated in dashed line by means of a piston/cylinder operator 589, one end of which is pivotally attached to a lug 590 on the plate 584 and the other end of which is pivotally attached to the extension 587 on the rocker arm 580.

Extension of the piston/cylinder operator 589 in the orientation shown in solid line in FIG. 17 urges the second stretch roll 578 into a generally vertical plane coincident with the first or lower stretch roll 576. In that position, the second stretch roll shaft 586 is parallel to the first stretch roll shaft 582. When the piston/cylinder operator 589 is retracted to the position shown in dashed lines in FIG. 17, the second stretch roll 578 is necessarily moved transversely of the path of the elastic band E and web W and the orientation of the second stretch roll shaft 586 necessarily tilts or becomes skewed with respect to the first stretch roll shaft 582.

The rocker arm 580, which carries both the first and second stretch rolls, is fixed to shaft 590 which is pivotally mounted to a support post 591. Post 591 has bifurcated end portions 592 and 593 receiving bearings 594 and 595, respectively, through which the shaft 590 is mounted for rotation.

As illustrated in FIG. 16, rocker arm 580 carries a cam follower or roller 596 which is adapted to engage a rotating cam 597 mounted to shaft 599 and supported for rotation on post 598. The shaft 599, and hence cam 597, are rotated at a constant angular velocity by a suitable means (not illustrated). Rotation of cam 597 causes the rocker arm 580 to swing or oscillate in an arc about the axis of shaft 590 toward and away from the pair of pinch rolls 556. This has the effect of elongating or relaxing the elastic band E extending between the stretch rolls 576 and 578 and the pinch rolls 556.

In order to maintain alternating stretched and unstretched segments of elastic band E as they are fed into the pinch rolls 556, an intermittently actuated braking or arresting system is provided. Specifically, a first brake means 510 is mounted to rocker arm 580 below the first stretch roll 576 and has a brake pad 512 which is adapted to be reciprocated between an extended position in contact with the band on roll 576 and a retracted position out of contact with the band E. Similarly, a second brake means 520 is mounted on the upper plate 584 and has a brake pad 522 adapted to be moved between an extended position in contact with the band E on roll 578 and a retracted position out of contact with the band E. The brake pads may be reciprocated between their extended and retracted positions by suitable conventional means, such as electric solenoid operators, pneumatic piston/cylinder operators, etc.

FIG. 18 illustrates the movement of the first and second stretch rolls 576 and 578 from the position furthest from the pair of pinch rolls 556 to the position closest to the pinch rolls 556. This movement is effected by the cam 597 causing the rocker arm 580 to swing in the direction of arrow 530. Immediately before this movement is initiated, and until the movement is terminated, the brakes 510 and 520 are applied to the rolls 576 and 578, respectively. Thus, as the rolls 576 and 578 are swung to the position closest to the pinch rolls 556, the linear distance through which the band E must travel before entering the pinch rolls 556 is reduced. This has the effect of relaxing a previously stretched band to form an unstretched segment of band.

Conversely, as the cam 597 rotates further, the rocker arm 580 swings back away from the pair of pinch rolls 556 as best illustrated in FIG. 19. At the inhibition of this return movement, and until the stretch rolls have been moved to the position furthest from the pinch rolls 556 in the direction of arrow 532, the brakes 510 and 520 are released. This allows the elastic band to continue feeding forward to the pinch rolls 556 even though the elastic band is being stretched. The movement of the stretch rolls illustrated in FIG. 19 thus elongates the elastic band and forms a stretched segment.

To provide the contoured configuration of the elastic band secured to the web as illustrated in FIG. 15, the piston/cylinder operator 589 (FIG. 17) is intermittently actuated. Of course, the movement of the piston/cylinder operator 589 is appropriately timed with the moving web to produce the desired configuration. It should also be noted that if desired, the first or lower stretch roll 576 could be mounted to an extension of the upper support member 584 (instead of to the lower support member 580 illustrated) so as to permit the lower roll 576 to tilt with the upper or second roll 578.

The band E is secured over all or a portion of its length to the web W by suitable means as previously described. For simplicity, such securing means have not been illustrated for this embodiment in FIGS. 16–19. Further, the assembled layer A, elastic band E, and web W may be severed downstream of the pair of rolls 556 at suitable intervals to form individual articles, such as diapers, by means of an appropriate severing mechanism 540 illustrated in FIG. 16.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

It is claimed:

1. The method of securing an elastic member to a flexible web of material defining diaper components comprising the steps of:
   (a) engaging a continuous strip of the elastic member with a rotating engaging member having an elastic member stretching first surface and an elastic member relaxing second surface, said first surface having a length greater than said second surface;
   (b) gripping a first region of said elastic member and continuing to rotate said engaging member against said strip of elastic member causing said elastic member to elongate about said first surface to form a stretched segment, gripping a second region of said elastic member to maintain the stretched segment in the stretched condition and continuing to rotate said engaging member causing said elastic member to relax against said second surface to form an unstretched segment;
   (c) moving said web along a path and feeding said segments along said path adjacent said web;
   (d) securing said stretched segment to a predetermined portion of said web; and
   (e) severing said web and said strip of elastic member generally transversely of said path whereby said unstretched segment imparts substantially no stretchable characteristic to said web and whereby said secured stretched segment contracts to gather the web of material to which it is secured for accommodating subsequent stretching.

2. The method of attaching an elastic member having stretched and relaxed portions to a diaper component comprising the steps of:
   (a) feeding an elastic member between two spaced sets of continuously operating feeding rolls being driven at a constant speed, the second set of rolls including a semi-cylindrical shaped stretching roll defining a curved stretching surface and a straight relaxing surface;
   (b) gripping a first region of said member on said stretching roll causing said member to elongate about said stretching surface to provide a stretched portion;
   (c) gripping a second region of said member to maintain the stretched portion in the stretched condition and whereby said member relaxes against said relaxing surface to form an unstretched portion;
   (d) moving said diaper component along a path and feeding said elastic member along said path adjacent said component;
   (e) securing a length of said elastic member having relaxed end portions and an intermediate stretched portion to said diaper component; and
   (f) severing said diaper component and elastic member in the area of the relaxed end portions of said secured length of elastic member.

3. The method of securing an elastic member to a flexible web of material defining diaper components comprising the steps of:
   (a) feeding a continuous strip of the elastic member at a constant linear speed to a rotating stretching member having a peripheral engaging surface and in a path guided around a portion of said engaging surface while rotating said stretching member at an angular velocity sufficient to impart a linear speed to said engaging surface greater than said elastic member feed speed;
   (b) applying a relaxed portion of said continuous strip of elastic member to said engaging surface of said rotating stretching member and gripping a first region of said elastic member on said stretching member to define an unstretched segment extending from said first region in the direction of rotation of said stretching member whereby;
   (c) gripping a second region of said elastic member on said stretching member to define and maintain a stretched segment around said stretching member between said two gripped regions;
   (d) severing the stretched elastic member exterior of said gripped regions of said stretched segment;
   (e) moving said web in a path and causing said segments to travel in said path adjacent said web; and
   (f) securing said stretched segment to a predetermined portion of said web
   whereby said unstretched segment imparts substantially no stretchable characteristic to said web and whereby said secured and stretched segment continues to gather the web of material to which it is secured for accommodating subsequent stretching.

4. The method in accordance with claim 3 including the further step (g) of severing said web.

5. The method in accordance with claim 4 in which said step (g) of severing said web includes substantially simultaneously also severing said elastic member in the area of an unstretched segment.

6. The method of attaching an elastic member having stretched and relaxed portions to a diaper component comprising the steps of:
   (a) feeding an elastic member between two spaced sets of continuously operating feeding rolls;
   (b) driving the first set of rolls at a peripheral speed less than that of the second set of rolls to provide a stretched elastic member therebetween;
   (c) gripping said stretched member at two spaced regions on one of said rolls of said second set and cutting the stretched member at a point exterior of and spaced from said gripped regions, thus providing spaced sections of an elastic member having relaxed end portions and an intermediate stretched portion;
   (d) moving said diaper component along a path and feeding said elastic member along said path adjacent said component;

(e) securing a length of the elastic member having relaxed end portions and an intermediate stretched portion to said diaper component; and (f) severing at least said diaper component at spaced locations.

7. The method of securing an elastic member to a flexible web of material defining diaper components comprising the steps of:

(a) feeding a continuous strip of the elastic member partially around a first roll in a first direction and partially around a second roll in a second, opposite direction to a pair of constant angular velocity pinch rolls;

(b) moving said first and second rolls in a fixed relationship away from said pinch rolls to elongate said elastic member to form a stretched segment and moving at least said second roll transversely from a position vertically coincident with said first roll to a tilted position;

(c) moving said web along a path and feeding said elastic member along said path adjacent said web;

(d) securing said stretched segment to a predetermined portion of said web;

(e) moving at least said second roll transversely to said position vertically coincident with said first roll, said first and second rollers in a fixed relationship towards said pinch roll to relax said elastic member to form an unstretched segment; and (f) severing said web and said strip of elastic member generally transversely of said path whereby each unstretched segment imparts substantially no stretchable characteristic to said web whereby said secured stretched segment contracts to gather the web of material to which it is secured for accommodating subsequent stretching.

8. An apparatus for attaching an elastic member having stretched and relaxed portions to a diaper component comprising:

(a) means for feeding an elastic member and a diaper component along a path;

(b) a semi-cylindrical shaped stretching roller disposed adjacent said elastic member, said roller defining a curved stretching surface and a straight relaxing surface, said roller having a first gripping means for gripping a region of said member at one end of said stretching surface and a second gripping means for gripping a region of said member at the other end of said stretching surface;

(c) means for rotating said stretching roller to engage a first region of said elastic member with said first gripping means as said elastic member elongates about said stretching surface and to engage a second region of said elastic member with said second gripping means to maintain a portion of said elastic member in the stretched condition around said stretching surface, whereby part of said elastic member subsequently lies against said straight relaxing surface to form an unstretched portion thereagainst;

(d) means for securing a length of said elastic member having relaxed end portions and an intermediate stretched portion to said diaper component; and (e) means for severing the diaper component and elastic member in the area of the relaxed end portions of said secured length of elastic member.

9. An apparatus for attaching an elastic member having stretched and relaxed portions to a diaper component comprising:

(a) means for feeding the elastic member and said diaper component along a path;

(b) first and second feed rolls adapted to feed the elastic ribbon therebetween;

(c) a stretching roll adjacent said second feed roll, said elastic member being passed between said second roll and said stretch roll and partially around the periphery of said stretch roll, said stretch roll having a first gripping means for gripping a first region of the elastic member and a second gripping means spaced from said first gripping means for gripping a second region of the elastic member, said stretching roll further having an outwardly projecting blade for intermittently severing the elastic member against said second roll, a first peripheral surface between said first and second gripping means comprising a member stretching surface, and a second peripheral surface comprising a member relaxing surface whereby rotation of said stretching roll brings said first gripping means into engagement with said elastic member and subsequently said second gripping means into engagement with said elastic member to define a stretched portion therebetween against said stretching surface and whereby continued rotation of said stretching roll brings said cutter blade into engagement with said elastic member against said second roll to sever said member causing relaxation of one severed end portion towards said first gripper means and relaxation of the other severed end portion towards said second gripper means;

(d) means for securing a length of the elastic member having relaxed end portions and an intermediate stretched portion to said diaper component; and (e) severing at least said diaper component at spaced locations.

10. The apparatus in accordance with claim 9 in which said stretching roll further includes first means for holding one of the relaxed end portions of said severed elastic member adjacent said first gripper means and in which said stretching roll further includes a second means for holding the other of the relaxed end portions of said severed elastic member adjacent said second gripper means.

11. The apparatus in accordance with claim 10 in which said first and second holding means include at least (1) a vacuum chamber within said stretching roll and (2) bores communicating between said vacuum chamber and the exterior surface of said stretching roll.

12. An apparatus for securing an elastic member to a flexible web of material in a non-linear configuration, said apparatus comprising:

(a) a pair of rotatable pinch rolls adapted to feed said elastic member and said web therebetween, said web traveling in fixed path through said pinch rolls;

(b) a drive roll for feeding said elastic member to said pinch rolls;

(c) a rocker arm disposed between said drive roll and said pair of pinch rolls and pivotally mounted for swinging movement toward and away from said pair of pinch rolls;

(d) first and second spaced apart stretch rolls mounted to said rocker arm, said elastic member being passed partially about the periphery of said first roll in one direction and partially about the periphery of said second stretch roll in the opposite direction;

(e) means for moving at least said second stretch roll transversely of the path of said web through pinch rolls between first and second transversely spaced positions;

(f) means for pivoting said rocker arm from a first position in which said stretch rolls are spaced a first distance from said pair of pinch rolls to a second position in which said stretch rolls are spaced a second distance, less than the first distance, from said pinch rolls;

(g) first brake means associated with said first stretch roll and second brake means associated with said second stretch roll, said first and second brake means adapted to engage said elastic member against their respective stretch rolls and prevent movement of said elastic member relative to said stretch rolls;

(h) first and second actuating means associated with said first and second brake means, respectively, for intermittently engaging said brake means when said rocker arm is moved from said first pivoted position to said second pivoted position and for releasing said brake means when said rocker arm is returned from said second pivoted position to said first pivoted position whereby alternating unstretched and stretched segments of said elastic member are formed;

(i) means for securing at least said stretched segments to predetermined portions of said web whereby transverse movement of said second stretch roll gives said stretched segment a non-linear shape as it is secured to said web; and (j) severing said web and said elastic member to separate a portion of said web with at least one stretched segment of said elastic member secured thereto.

* * * * *